(12) United States Patent
Jones

(10) Patent No.: US 8,720,436 B2
(45) Date of Patent: May 13, 2014

(54) NITRIC OXIDE GEL APPARATUS AND METHOD

(75) Inventor: Christie M. Jones, Chula Vista, CA (US)

(73) Assignee: Genosys, Inc., Orem, UT (US)

( * ) Notice: Subject to any disclaimer, the term of this patent is extended or adjusted under 35 U.S.C. 154(b) by 728 days.

(21) Appl. No.: 12/361,123

(22) Filed: Jan. 28, 2009

(65) Prior Publication Data
US 2010/0021506 A1    Jan. 28, 2010

Related U.S. Application Data

(60) Provisional application No. 61/025,226, filed on Jan. 31, 2008.

(51) Int. Cl.
| | |
|---|---|
| *A61M 16/10* | (2006.01) |
| *C01B 21/24* | (2006.01) |
| *A61K 9/72* | (2006.01) |
| *A61K 31/194* | (2006.01) |
| *A61K 31/375* | (2006.01) |
| *A61K 47/16* | (2006.01) |

(52) U.S. Cl.
USPC ............... 128/202.26; 128/200.24; 424/718; 514/566; 514/574

(58) Field of Classification Search
CPC ....... A61M 16/10; A61K 9/72; A61K 31/194; A61K 31/375; A61K 33/00; A61K 47/16; C01B 21/24
See application file for complete search history.

(56) References Cited

U.S. PATENT DOCUMENTS

| | | | |
|---|---|---|---|
| 5,427,797 A | 6/1995 | Frostell et al. | |
| 5,485,827 A * | 1/1996 | Zapol et al. | ............ 128/200.14 |
| 5,713,349 A | 2/1998 | Keaney | |
| 5,823,180 A | 10/1998 | Zapol | |
| 5,839,433 A | 11/1998 | Higgenbottam | |
| 5,873,359 A | 2/1999 | Zapol | |
| 6,000,403 A | 12/1999 | Cantwell | |
| 6,019,100 A | 2/2000 | Alving et al. | |
| 6,063,407 A | 5/2000 | Zapol et al. | |
| 6,103,275 A * | 8/2000 | Seitz et al. | .................. 424/718 |
| 6,131,572 A | 10/2000 | Heinonen | |
| 6,142,147 A | 11/2000 | Head et al. | |
| 6,149,606 A | 11/2000 | Alving et al. | |
| 6,432,077 B1 | 8/2002 | Stenzler | |
| 6,458,109 B1 | 10/2002 | Henley et al. | |
| 6,572,594 B2 | 6/2003 | Satterfield et al. | |
| 6,581,599 B1 | 6/2003 | Stenzler | |
| 6,601,580 B1 | 8/2003 | Bloch et al. | |
| 6,612,306 B1 | 9/2003 | Mault | |
| 6,670,323 B1 | 12/2003 | Looker et al. | |
| 6,786,217 B2 | 9/2004 | Stenzler | |

(Continued)

FOREIGN PATENT DOCUMENTS

| | | |
|---|---|---|
| WO | 2006/110923 | 10/2006 |
| WO | 2007/057763 | 5/2007 |

*Primary Examiner* — Ernst Arnold
(74) *Attorney, Agent, or Firm* — Pate Baird, PLLC

(57) ABSTRACT

Gel strips containing reactants capable of reacting to form nitric oxide are maintained separate until application. Upon application, the gel strips are placed in contact with one another, and may mix, or operate by diffusion, to deliver nitric oxide directly to the stream of breathing air of a user. Adhesive strips bonded to a substrate supporting the gel strips may provide for securing the nitric oxide generator directly to an upper lip of a user for breathing the nitric oxide through the nostrils.

20 Claims, 6 Drawing Sheets

(56) References Cited

U.S. PATENT DOCUMENTS

| | | |
|---|---|---|
| 6,793,644 B2 | 9/2004 | Stenzler |
| 7,017,573 B1 | 3/2006 | Rasor et al. |
| 7,045,152 B2 | 5/2006 | Stamler |
| 7,122,018 B2 | 10/2006 | Stenzler et al. |
| 2007/0059351 A1* | 3/2007 | Murrell et al. ............ 424/449 |

* cited by examiner

NITRIC OXIDE GEL APPARATUS AND METHOD

RELATED APPLICATIONS

This application claims the benefit of co-pending U.S. Provisional Patent Application Ser. No. 61/025,226, filed on Jan. 31, 2008.

BACKGROUND

1. The Field of the Invention

This invention relates to treatments providing nitric oxide as a vasodilator, and, more particularly, to delivery of gaseous nitric oxide by inhaling.

2. Background

The discovery of the nitric oxide effect in live tissues garnered a Nobel prize. Much of the work in determining the mechanisms for implementing and the effects of nitric oxide administration are reported in literature including papers, advertising, catalogs, and patents. Much of the work deals with introduction of substances that provide a nitric oxide effect in the body. Still other applications may involve topical preparations introducing nitric oxide. Still other applications rely on bottled nitric oxide gas. Introduction of nitric oxide to the human body has traditionally been expensive.

The therapies, compositions, and preparations are sufficiently expensive to inhibit more widespread use of such therapies. What is needed is a comparatively inexpensive mechanism for introducing nitric oxide in a single dosage over a predetermined period of time. Also, what is needed is a simple introduction method for providing nitric oxide suitable for inhaling.

BRIEF SUMMARY OF THE INVENTION

In accordance with the foregoing, certain embodiments of an apparatus and method in accordance with the invention provide a reactive kit having two compounds, typically disposed in carriers. The two compounds are separated from one another prior to administration. In order to administer the nitric oxide, gel strips are placed in communication with one another beginning a reaction releasing nitric oxide.

An adhesive member may secure the gel strips to a mask or directly to the skin of a user, proximate the nose. A predetermined rate or amount of nitric oxide may thus be introduced into the breathing air of a subject. Nitric oxide amounts may be engineered to deliver at a comparatively low rate in the hundredths of parts per million, or in a therapeutically effective amount on the order of thousands of parts per million. For example, sufficient nitric oxide may be presented through nasal inhalation to provide approximately five thousand parts per million in breathing air. This may be diluted again (e.g., to about 1200 parts per million) due to additional breathing bypass through nasal inhalation or through oral inhalation.

Some embodiments of an apparatus and method in accordance with the present invention may rely on a layered system having an adhesive strip for securing to an upper lip of a user. A substrate may secure to one side of the adhesive strip while a backing paper, easily removable, may be secured to the opposite side of the adhesive strip. The substrate may support a gel compounded having an appropriate moisture content to support migration of reactants by diffusion therethrough while still maintaining a suitable degree of mechanical integrity. A texture or other holder configuration on a surface of the substrate may support or secure the gel composition.

A second composition in a gel carrier may be sealed or otherwise separated from the first gel composition. For example, the two gel strips may be contained in separate packages. Alternatively, the two gel strips may simply be appropriately separated by an intervening layer, such as a film, paper, or the like. The second layer of gel may be mounted on a substrate as a mechanical integrity precaution, as a mechanism to reduce exposure to ambient air, or both. The first gel strip may be secured by way of the adhesive strip on its substrate to an upper lip of a user. The second gel strip may then be opened and placed in contact with the first gel strip to permit combination of the reactants needed to form nitric oxide. In one embodiment, the reactants may include an acid, such as ascorbic acid, citric acid, or the like. The other reactant may include potassium nitrite.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
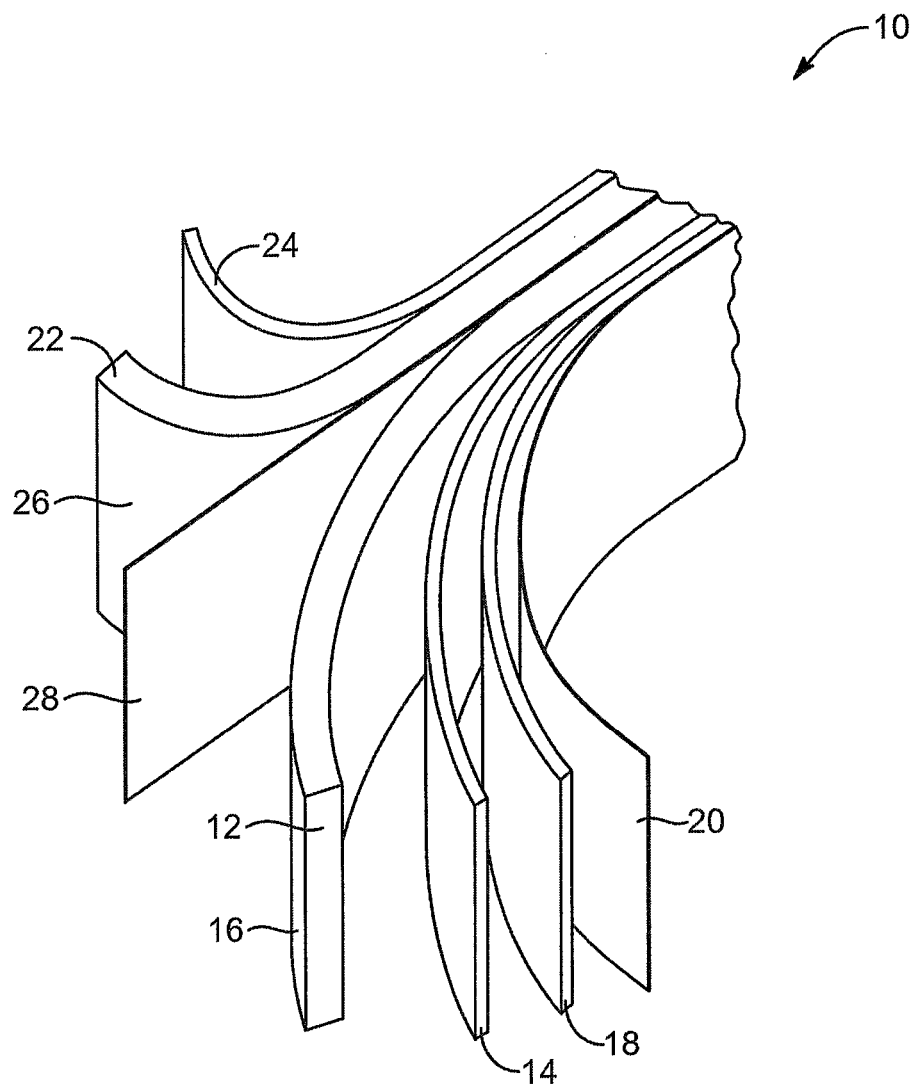
FIG. 1 is a perspective view of one embodiment of a layup of layers in one apparatus in accordance with the invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, in one embodiment of an apparatus and method in accordance with the invention, an apparatus 10 may involve a composition formed as a gel layer 12 to have dimensions of thickness, width, and length suitable for creating and sustaining a reaction of an ingredient carried in the carrier gel. For example, a reactive material may be dissolved in a liquid stabilized by gelling agents. Alternatively, reactants may be disposed at a comparatively higher concentration along a surface of a gel carrier.

Meanwhile, the gel carrier may provide sufficient transport for migration of molecules of a reacting composition in order to provide a reactant output. In certain embodiments, the gel may be comparatively thicker in order to provide additional mechanical strength. In other embodiments, the gels may be effectively thixotropic but containing very high levels of hydration, such as fifty to ninety percent water or more. Accordingly, the liquids provide for a concentration gradient to develop, driving each reactant toward the opposing reactant.

The composition 12 or gel strip 12 may be secured to a substrate 14. The substrate 14 may also include texturing 15 or holders 15 disposed thereon to mechanically stabilize the gel layer 12, as shown more particularly in FIG. 2. The reacting surface 16 or simply the surface 16 of the gel strip 12 may be sealed to prevent exposure to oxygen prior to implementation of a method in accordance with the invention.

On a surface of the substrate 14 opposite the position of the gel strip 12, an adhesive 18 or a layer 18 of adhesive may be applied. The thickness of the layer 18 may be selected to provide securement to an interior surface of a mask, an upper lip of a user, or the like. Various adhesives may be selected to provide adequate securement while also providing suitable release force requirements. Prior to deployment, the adhesive 18 may be covered with a cover 20 or backing 20. For example, paper treated with a polymer to reduce adhesion to the adhesive layer 18 may form the backing 20.

Similar to the gel strip 12, a second composition 22 or gel strip 22 may be positioned to face the initial gel strip 12. Likewise, this new gel layer 22 may be deposited on a substrate 24, with or without holders 25 or texturing 25, as shown more particularly in FIG. 2, to secure compliance of the gel layer 22 with the substrate 24.

A surface 26 of the gel layer 22 operates as both a contact surface 26, and a reaction surface 26 at which, or across which, the reactant species migrate in order to contact one another and react to provide the nitric oxide output of the apparatus 10.

A divider layer 28 may contact the surface 16 of the first gel layer 12, as well as the surface 26 of the second gel layer 22. The two gel layers 12, 22 need not be packaged in the same assembly prior to being placed in contact with one another to begin the desired reaction. However, in one embodiment, a divider layer 28 may be placed in between. Accordingly, the divider layer 28 may be removed from one of the surfaces 16, 26, and then removed from the other surface 26, 16 in order to be thrown away. Thereafter, the two surfaces 16, 26 may be placed in contact with one another, thus initiating the reaction to produce nitric oxide for inhaling. In a typical embodiment, the adhesive layer 18 may be secured to the skin of a user such as just under the nose. In an alternative embodiment, a mask covering the nose, mouth, or both may receive the adhesive 18 in proximity to the nose in order to provide a preselected dose of nitric oxide for inhaling.

In one embodiment of an apparatus and method in accordance with the invention, a mask may be provided with a one-way valve such that breathing out through the mask will not pass air over the apparatus 10, and will thus not discharge nitric oxide overboard. Upon air intake in inhalation, the one-way valve (e.g., flapper valve, check valve, or the like) will open, drawing air past the apparatus 10, and introducing the desired quantity of nitric oxide in the stream of breathing air.

It has been determined that a gram of the first gel 12 placed in contact with a gram of a second gel 22, each containing a suitable quantity of an acid such as ascorbic acid or citric acid, while the opposite layer contains a corresponding amount of potassium nitrite, will provide a quantity of more than five thousand parts per million of nitric oxide in breathing air for over half an hour. With bypass air, this typically dilutes to about twenty-five percent of the original inhaled concentration. Thus, over twelve hundred parts per million in the air of the lungs may be maintained for a time of about thirty minutes.

Figure 3:
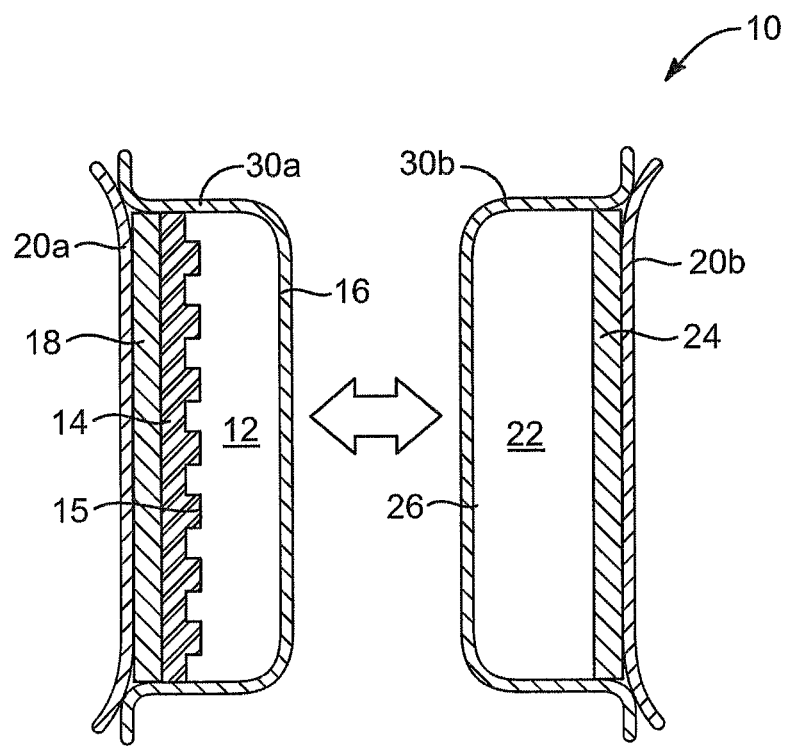
FIG. 3 is an end, cross-sectional view of an alternative embodiment of a two-part apparatus for introducing nitric oxide from reacting gels in accordance with the invention.

Referring to FIG. 3, an apparatus 10 may be configured in multiple pieces. For example, in the illustrated embodiment, the apparatus 10 may contain one gel layer 12 on its substrate 14, with or without holders 15 or texturing 15 on the substrate 14 to hold the gel layer 12. In such an embodiment, the adhesive 18 is mounted to the substrate 14 opposite the gel layer 12. Meanwhile, a cover 20a or backing 20a may cover the adhesive 18 in order to maintain cleanliness and the like.

Meanwhile, another cover 30a may be applied to seal the exposed outer surface 16 of the gel layer 12, as well, against the atmosphere and environment. In certain embodiments, the cover 30a may be sealed to the backing 20a in order to provide a completely sealed package. The substrate 14 may be configured to provide additional support or sealing along the bottom and end thereof. For example, in the illustrated embodiment, the cross-sectional view illustrates a bottom portion of the substrate 14 that may serve to support and seal that portion of the substrate 14 and gel strip 12 against oxygen, even in use.

Meanwhile, the substrate 24 corresponding to the gel layer 22 may have a similar configuration to matingly engage the substrate 14 and to place the gel layer 22 in contact with the gel layer 12.

For example, the surface 16 may be placed in contact with the surface 26 of the gel layer 22. Meanwhile, the backing 20b need only serve as a mechanism to seal the cover 30b around the gel layer 22.

Figure 2:
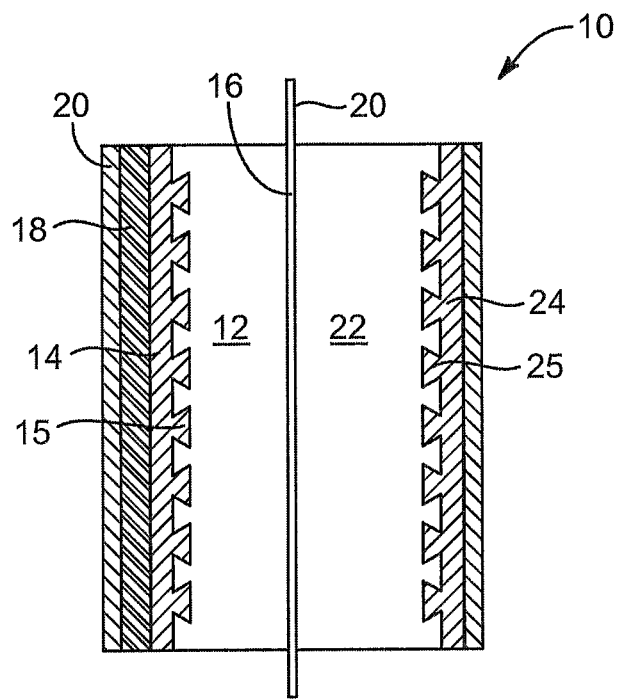
FIG. 2 is an end, cross-sectional view of an apparatus in accordance with FIG. 1.

The layups illustrated in FIGS. 1-3 may typically begin with a selection of reactants, followed by providing a suitable substrate. Reactants may include, for example, an acid of modest strength such as citric acid or ascorbic acid. Meanwhile, such an acid may react appropriately with potassium nitrite. Other nitrogen compounds may also serve. In certain embodiments, the reactants may be provided as solids. In other embodiments, the reactants may be provided as solutions in a liquid, such as water. In yet other embodiments, the reactants may be provided in a solution mechanically stabilized as a gel, such as a water-based gel.

Providing a substrate may include selecting a material to operate with the gel layers 12, 22. The reactants may be mixed with the gel in order to provide a solution. Alternatively, the reactants may be mixed dry, and a liquid or gel may be introduced in order to carry chemical species and ions during reaction.

The layups may be created by providing the gel composition, for each of the gel layers 12, 22, and disposing them along the substrates 14, 24, respectively. Adhesive may be added behind the substrate 14 at any appropriate time, and the sealing covers 20, 30 may be added thereafter. The development of the apparatus 10 may begin with removal of both seals or covers 20, 30, by separation from one another.

By positioning the surfaces 16, 26 against one another, the reactants may begin to react. In certain embodiments, the shape of the surfaces 16, 26 may be designed to promote a certain degree of mixing therebetween upon contact. For example, the surfaces 16, 26 may actually be formed to be smooth, splined, undulating, saw-toothed, or the like.

Accordingly, introducing the two gel layers 12, 22 to one another may actually involve mixing them with one another.

After the gel strips 12, 22 are unsealed and placed in contact, they may be deemed activated. The adhesive 18 may then be applied to the skin of a user proximate the nose, or mouth. Likewise, the adhesive may be used to retain the apparatus 10 against the interior of a breathing mask. Breathing masks are available in the art and are used for oxygen provision, continuous positive airway pressure apparatus, and the like.

The reactants in the gel strips 12, 22 have been found to provide adequate levels of nitric oxide production. For example, a gram of gel 12 combined with a gram of gel 22 have been found to provide a five thousand parts per million dose for over thirty minutes to a user.

As the reactants are eventually consumed, the rate of production of nitric oxide may decay to a useless level. Below some threshold value, the apparatus 10 may be deemed inappropriate or expended. Accordingly, the adhesive 18 may be removed from its location during deployment and the apparatus 10 may be disposed of appropriately.

Figure 4:
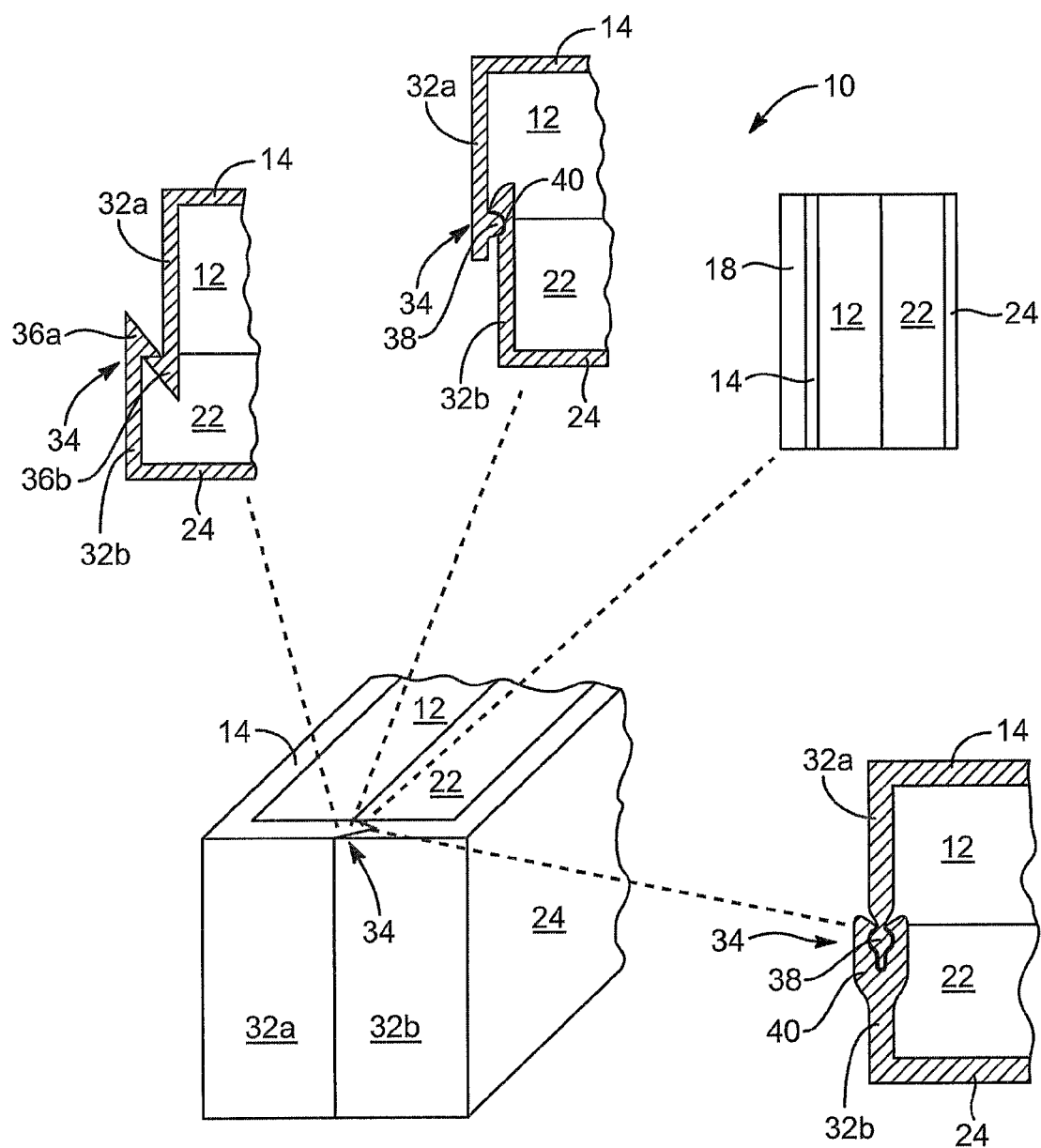
FIG. 4 is a top plan view of one embodiment of a mechanism for connecting the substrates under the gel strips in accordance with the invention.

Referring to FIG. 4, in certain embodiments of an apparatus 10 in accordance with the invention, the substrates 14, 24 may mechanically engage one another to provide selected sealing and opening. For example, in the contemplated deployment directly near a breathing opening (e.g., nostrils, mouth), it may be desirable to permit the nitric oxide production to exit only in a single direction.

This also has the effect of sealing other surfaces against additional reaction with available environmental oxygen. For example, if oxygen is allowed to come in contact with the nitric oxide, the nitric oxide may become nitrogen dioxide, or some other compound of nitrogen. Although these compounds may not be harmful, any overreaction creating a compound of nitrogen having more than a single oxygen for each nitrogen atom is a waste of reactant material.

Accordingly, the substrate 14 may be formed as a latching structure, having ends 32, having an engagement mechanism 34 to seal them together. For example, a barb or ratchet-like connection may provide that once the two substrates 14, 24 have engaged to within a certain proximity, they will be latched together by the latching device 34. In other embodiments, a detent such as a bump, corrugation, boss, or the like may be designed to engage a recess in a corresponding substrate 24.

For example, in the left central illustration of the alternative embodiments of FIG. 4, a detent is engaged by a recess. In the leftmost embodiment, a ratchet or barb engages the two substrates 14, 24 with one another. In the right central embodiment, the adhesive properties of the gel layers 12, 22 themselves nearly maintain themselves in contact.

In such an embodiment, the outer edges of the gel layers 12, 22 may be treated with an oil, a film, a non-reactant substance, another polymer, or the like. Nevertheless, the gel layers 12, 22 are not sealed so firmly as in the other embodiments. Likewise, in the embodiment of FIG. 4, the rightmost illustration shows a detent in which a receiver receives a detent, capturing the detent from both sides thereof. Typically, a barb 36*a* may be used opposite another barb 36*b* relying only on the resilience of the material of the substrates 14, 24, respectively. Typically, a detent 38 may operate with respect to a relief 40 in a corresponding piece by the same manner. However, in certain embodiments, a more affirmative (e.g., forceful) bonding may occur if the detent 38 is fully captured by the relief 40 completely surrounding the detent 38 as illustrated in the rightmost illustration.

Figure 5:
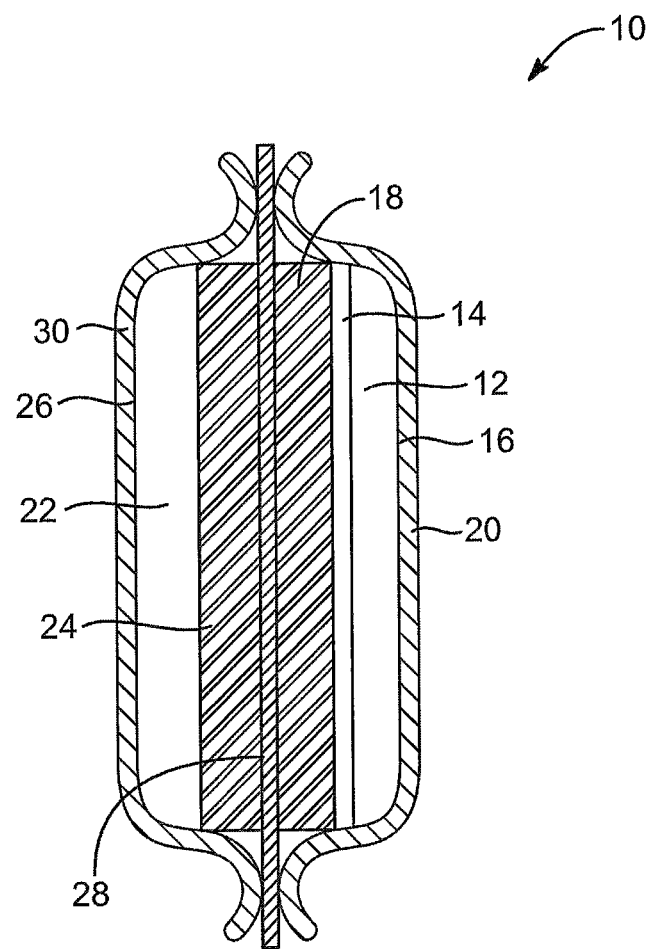
FIG. 5 is an end, cross-sectional view of one embodiment of a packaging scheme for one embodiment of an apparatus in accordance with the invention.

Referring to FIG. 5, in certain embodiments, a single package may implement the apparatus 10 in one embodiment. In the illustration of FIG. 5, a gel layer 12 is disposed on a substrate 14 provided with an adhesive 18. The surface 16 is sealed by the cover 20. Meanwhile, a gel layer 22 is disposed along the substrate 24, having its reaction surface 26 sealed by a cover 30.

Meanwhile, a divider 28, operates in a manner almost opposite that of the divider 28 of FIGS. 1-2. In FIGS. 1-2 the divider serves to separate the gel layers 12, 22. In the illustrated embodiment FIG. 5, the divider 28 serves to divide two packages, each separately sealed between its respective cover 20, 30, and the divider 28. Thus, the adhesive 18 may be peeled from the divider 28, as described hereinabove.

Meanwhile, the substrate 24 may be removed from the divider 28, and the surfaces 16, 26 may be juxtaposed and placed in contact. In certain embodiments, the substrate 24 may act as the divider 28. However, one benefit of having the divider 28 as a separate element is that it may extend beyond the operational dimensions of the gel layers 12, 22, and their respective substrates 14, 24, in order to effect the seals with the respective covers 20, 30.

Figure 6:
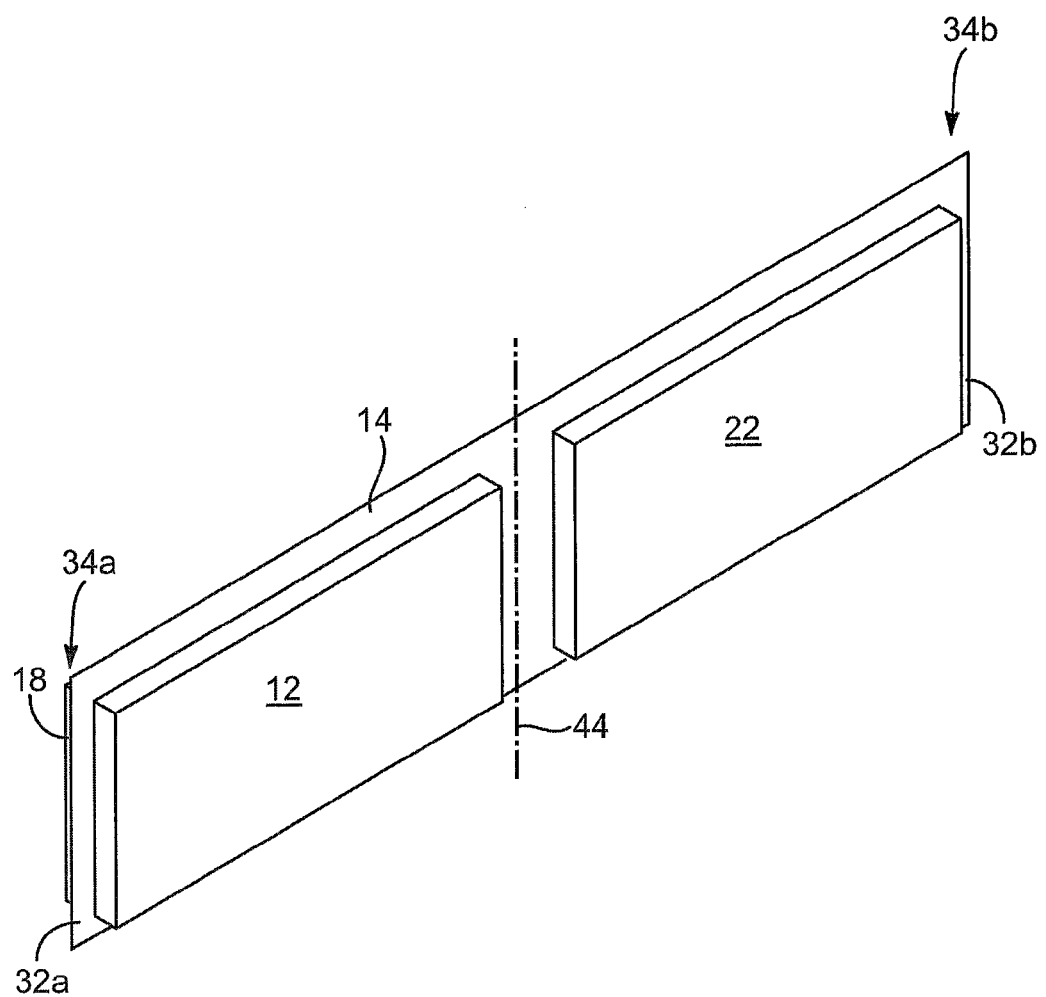
FIG. 6 is a perspective view of one embodiment of an alternative, single-substrate apparatus formed in a method in accordance with the invention.

Referring to FIG. 6, in one embodiment of an apparatus and method in accordance with the invention, an apparatus 10 may be formed on a single substrate 14. In this embodiment, the packaging may be that reflected in FIG. 3, FIG. 5, or an alternative packaging. In the illustrated embodiment, the gel layers 12, 22 may be maintained separately from one another in order to prevent any premature reaction. Meanwhile, upon removing any covers 20, 30 from the gel layers 12, 22, the substrate 14 may be folded about a fold line 44 near the center thereof, placing the gel strips 12, 22 in contact with one another along their reaction surfaces 16, 26, respectively.

In the illustrated embodiment, the ends 32*a*, 32*b* may be provided with a latch device 34, such as a barb 36, detent 38 and relief 40, or the like, as illustrated hereinabove. The adhesive layer 18, may be applied to the substrate 14 opposite the gel layer 12. The use of a latching device 34 along with the substrate being bent about the fold line 44 may maintain the gel strips 12, 22, in close proximity for reaction purposes.

Figure 7:
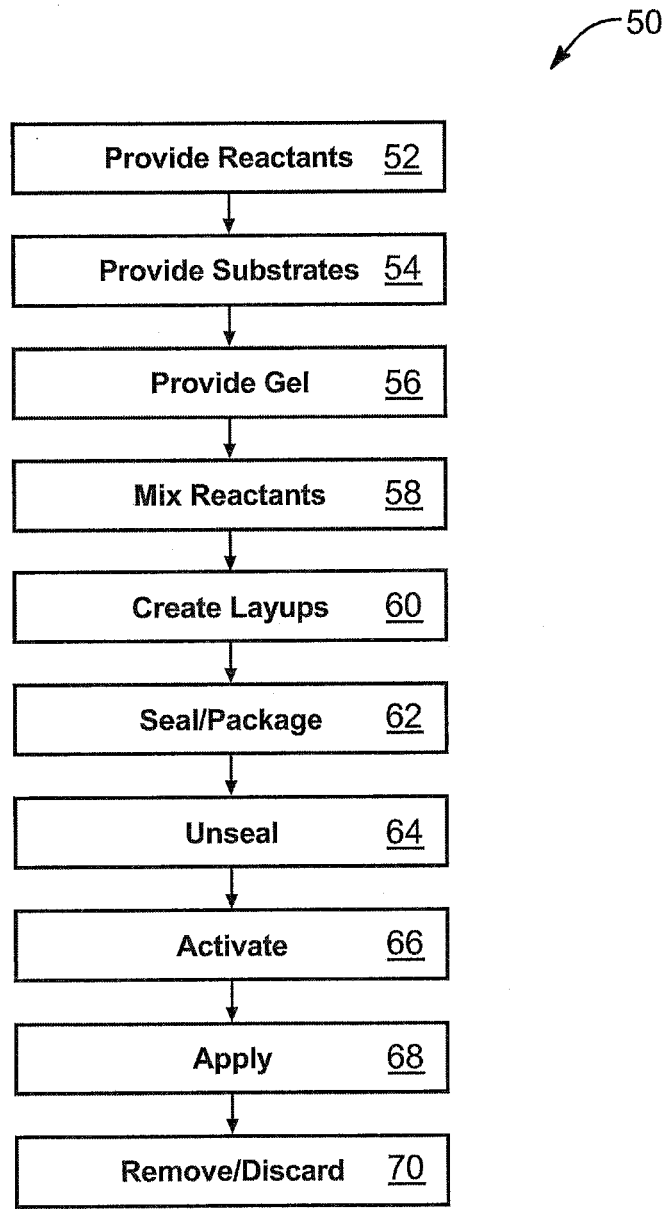
FIG. 7 is a schematic block diagram of one embodiment of a method in accordance with the invention.

Referring to FIG. 7, one embodiment of an apparatus and method in accordance with the invention may rely on a process 50, or some part thereof. For example, providing 52 reactants may be done by providing solids, granules, powders, or the like sufficiently dry that there is very little reactivity therein. Likewise, providing 52 reactants in a liquid or gel provides an enabler, a transport medium or carrier to carry either a particulate or a dissolved reactant. Reactants typically provided may include a carrier such as water, another liquid, a gel, or the like, along with an acid, such as citric acid or ascorbic acid, and a compound of nitrogen such potassium nitrite.

Providing 54 a substrate may involve providing a material to support the reactants. Typical substrates may include fabric soaked in a reactant, a batting, such as cotton or a synthetic bat, a strip, a box, or the like. Providing 56 a gel may involve gelling a solution already containing a reactant, or providing a carrier material for receiving a reactant. Other embodiments may use other mechanisms to introduce, and separate or mix an active ingredient from a carrier gel. By gel is meant simply a stabilized liquid that is mechanically capable of supporting its weight. Gels may range from thixotropic fluids to rheological solids with viscoelastic properties.

Mixing 58 the reactants may involve mixing the reactants with one another, mixing the reactants with a gel, or otherwise providing them in a disposition suitable for ready application. Creating 60 the layups may involve the processes described hereinabove for providing the gel layers 12, 22 on the substrates 14, 24, respectively, along with their respective covers 20, 30, and the like.

Sealing 62 may involve using the covers, other materials, coatings, films, and the like, including foils, plastics, oils, and the like to seal the reactants against the environment and against one another.

During deployment, a user will typically unseal 64 a package containing the apparatus 10. Activation 66 typically involves placing the reactants in contact with one another. This may be done chemically or mechanically. For example, the gel layers 12, 22 may be disposed with respect to one another as described hereinabove. The gel layers may be placed in contact. They may be forced into one another. They may be shaped in such a way that there tends to be mixing. They may be placed in proximity to one another and then mixed somewhat with one another, or the like.

Accordingly, the active ingredients may be activated 66 to begin their reaction with one another, producing nitric oxide in the process. Applying 68 the apparatus 10 to a user for purposes of therapy may involve simply securing the adhesive 18 to the body of a user near the nostrils in order to promote breathing of the nitric oxide as it is generated.

After a preselected period of time for dosing, or upon expiration of the active ingredients, the apparatus 10 may be removed 70 from a user. Inasmuch as nitric oxide and nitrogen dioxide have the tendency to color the gels 12, 22, the presence of a dark rust or dark brown color indicates that the reactants are used up. Is has been observed that the gel will initially create a white froth as gases are generated within the gel. Eventually, a pink color overtakes the white reflection of a refraction of light from the air bubbles. The pink color eventually gives way to brown, which eventually becomes dark brown.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method for inhalation therapy of a user, the method comprising:
    providing first and second reactants capable together of producing nitric oxide;
    providing a substrate having first and second surfaces;
    disposing an adhesive on one of the first and second surfaces;
    providing a gel, adherent to the substrate;
    mixing the first reactant into a first layer formed of the gel;
    mixing the second reactant into a second layer formed of the gel;
    disposing at least one of the first and second layers on the other of the surfaces;
    providing a first seal containing the first layer;
    providing a second seal containing the second layer;
    providing the substrate and the first and second layers together connected in proximity to one another;
    providing instructions directing engagement of the first and second layers thereby producing at least 5,000 ppm of nitric oxide over a period of at least 30 minutes;
    providing instructions directing adhesion of the adhesive on an upper lip of a user proximate the nostrils of the user for inhalation therapy.

2. The method of claim 1, further comprising:
    providing instructions directing removal of the first and second seals.

3. The method of claim 2, wherein at least one of the first and second seals is disposed between the first and second layers.

4. The method of claim 3, further comprising:
    forming lay ups comprising the first and second layers, the adhesive, the substrate, and the first and second seals adjacent one another and separating the first and second layers from contacting one another.

5. The method of claim 4, further comprising:
    providing a third seal;
    placing the third seal over the adhesive; and
    providing instructions to a user directing removal of the third seal before placement of the adhesive on the upper lip of the user.

6. The method of claim 3, further comprising:
    providing a third seal;
    placing the third seal over the adhesive; and
    providing instructions to a user directing removal of the third seal before placement of the adhesive on the upper lip of the user.

7. The method of claim 1, further comprising:
    providing a third seal;
    placing the third seal over the adhesive; and
    providing instructions to a user directing removal of the third seal before placement of the adhesive on the upper lip of the user.

8. The method of claim 1, further comprising:
    exposing the first gel layer to the second gel layer to activate a reaction between the active ingredients therein;
    positioning the adhesive layer on the skin of a user proximate the nostrils thereof; and
    exposing the nostrils of a user to nitric oxide generated by reaction of the first and second reactants in the first and second layers.

9. The method of claim 8, further comprising:
    removing from a user the substrate and first and second layers after at least one of:
    expiration of the first or second reactant; and
    a preselected time selected for a dosing.

10. A method of inhalation therapy comprising:
    providing a substrate having first and second surfaces;
    providing at least first and second reactants, selected to form nitric oxide upon exposure to one another in a transport carrier;
    providing a gel as a transport carrier;
    mixing the at least first reactant in a first portion of the gel;
    mixing the at least second reactant in a second portion of the gel;
    forming the first portion into a first layer;
    forming the second portion into a second layer;
    preventing chemical reaction of the at least first and second reactants by separating the first and second layers from one another;
    disposing at least one of the first and second layers on a first surface;
    disposing an adhesive on the second surface;
    sealing the assembly comprising the substrate and first and second layers; and
    breaking the sealing;
    creating nitric oxide by exposing the at least first reactant and at least second reactant to one another thereby producing at least 5,000 ppm of nitric oxide over a period of at least 30 minutes; and administering the nitric oxide as a therapeutic inhalant to a user.

11. The method of claim 10 further comprising:
providing instructions effective to combine the first and second layers.

12. The method of claim 10, further comprising providing instructions effective to initiate a reaction between the at least first and second reactants by exposing the first and second layers to one another.

13. The method of claim 10, wherein separating the first and second layers further comprises sealing the first and second layers in separate volumes.

14. The method of claim 10, further comprising providing instructions effective to instruct a user to place the adhesive on the skin of a user.

15. The method of claim 14, further comprising providing instructions effective to instruct a user how to unseal at least one of the adhesive, the first layer, and the second layer.

16. The method of claim 15, further comprising providing instructions effective to instruct a user how to position the substrate to expose the nostrils of a user to intake a does of nitric oxide generated by the first and second layers.

17. The method of claim 16, further comprising providing instructions effective to instruct a user how to terminate a dosing upon occurrence of at least one of expiration of at least one of the at least first and second reactants, and a preselected time corresponding to the dosing.

18. A method of inhalation therapy comprising:
acquiring an apparatus comprising
a substrate,
a first layer of a gel, disposed on the substrate,
a second layer of the gel, disposed near the substrate and spaced from the first layer,
a separator separating the first and second layers chemically,
the first and second layers containing respective first and second reactants selected to produce nitric oxide upon exposure to one another,
at least one seal separating the first and second layers from the surrounding environment, and
an adhesive disposed on the substrate opposite the first layer,
adhering the adhesive to the skin of a user;
exposing the first and second reactants to one another by moving the separator;
inhaling nitric oxide provided by the first and second reactants as a therapeutic inhalant wherein the concentration of inhaled nitric oxide is approximately 1200 ppm over a period of approximately 30 minutes.

19. The method of claim 18, further comprising removing the adhesive from the skin of the user upon occurrence of at least one of expiration of a preselected time corresponding to dosing for the nitric oxide, and substantial completion of the reaction of at least one of the first and second reactants.

20. The method of claim 19, wherein the first reactant is selected from citric acid, ascorbic acid, and mixture thereof, and the second reactant is potassium nitrite.

* * * * *